United States Patent
Nam et al.

(10) Patent No.: US 10,766,887 B2
(45) Date of Patent: Sep. 8, 2020

(54) BENZOXAZINE-BASED MIXTURE AND USE THEREOF

(71) Applicant: KOLON INDUSTRIES, INC., Seoul (KR)

(72) Inventors: Sae Rom Nam, Yongin-si (KR); Do Kyung Sung, Yongin-si (KR); Hee Jin Cho, Yongin-si (KR)

(73) Assignee: KOLON INDUSTRIES, INC., Seoul (KR)

( * ) Notice: Subject to any disclaimer, the term of this patent is extended or adjusted under 35 U.S.C. 154(b) by 0 days.

(21) Appl. No.: 16/312,650

(22) PCT Filed: Jun. 30, 2017

(86) PCT No.: PCT/KR2017/006939
§ 371 (c)(1),
(2) Date: Dec. 21, 2018

(87) PCT Pub. No.: WO2018/004289
PCT Pub. Date: Jan. 4, 2018

(65) Prior Publication Data
US 2019/0169177 A1    Jun. 6, 2019

(30) Foreign Application Priority Data

Jun. 30, 2016 (KR) .......... 10-2016-0082246

(51) Int. Cl.
| C07D 413/10 | (2006.01) |
| C07D 265/16 | (2006.01) |
| C07D 265/14 | (2006.01) |
| C08G 73/02 | (2006.01) |
| C07D 413/14 | (2006.01) |
| C08L 79/04 | (2006.01) |

(52) U.S. Cl.
CPC ......... *C07D 413/10* (2013.01); *C07D 265/14* (2013.01); *C07D 265/16* (2013.01); *C07D 413/14* (2013.01); *C08G 73/02* (2013.01); *C08L 79/04* (2013.01)

(58) Field of Classification Search
CPC .................................................. C07D 413/10
USPC ........................................................ 544/90
See application file for complete search history.

(56) References Cited

FOREIGN PATENT DOCUMENTS

| CN | 101831073 A | 9/2010 |
| EP | 2 395 059 A1 | 12/2011 |
| JP | 2000-017146 A | 1/2000 |
| JP | 2000-086863 A | 3/2000 |
| JP | 2000-178332 A | 6/2000 |
| JP | 2003-082099 A | 3/2003 |
| KR | 10-2014-0086108 A | 7/2014 |
| WO | 2008/034814 A2 | 3/2008 |
| WO | 2015/130464 A1 | 9/2015 |

OTHER PUBLICATIONS

International Search Report of PCT/KR2017/006939 dated Dec. 12, 2017.

*Primary Examiner* — Kahsay Habte
(74) *Attorney, Agent, or Firm* — Sughrue Mion, PLLC

(57) ABSTRACT

The present invention relates to a benzoxazine-based mixture and a use thereof and, more specifically, to a benzoxazine-based mixture and a use of a cured product in which the benzoxazine-based mixture is cured, wherein the benzoxazine-based mixture has high dielectric characteristics, heat resistant characteristics, and flame-retardant characteristics by comprising a benzoxazine ring in a molecular structure, and thus can be applied to a sealing material, a molding material, a template material, an adhesive, a material for an electric insulation paint, and the like, which are used for a copper clad laminate or an electronic part, used in a printed circuit board.

11 Claims, No Drawings

BENZOXAZINE-BASED MIXTURE AND USE THEREOF

CROSS REFERENCE TO RELATED APPLICATIONS

This application is a National Stage of International Application No. PCT/KR2017/006939 filed Jun. 30, 2017, claiming priority based on Korean Patent Application No. 10-2016-0082246 filed Jun. 30, 2016.

TECHNICAL FIELD

The present invention relates to a benzoxazine-based mixture having excellent heat resistance and electrical characteristics and its use.

BACKGROUND ART

Conventionally, thermosetting resins such as phenol resin, melamine resin, epoxy resin, unsaturated polyester resin and bismaleimide resin are widely used in a wide variety of industries because of having thermosetting property and its excellent water resistance, chemical resistance, heat resistance, mechanical strength and reliability.

However, there are drawbacks that phenol resins and melamine resins generate volatile by-products upon curing and epoxy resins and unsaturated polyester resins have poor flame retardancy and bismaleimide resins are very expensive.

In order to solve these drawbacks, polybenzoxazine which is thermally cured without involving the generation of volatile components has been studied.

Benzoxazine has a complex structure of benzene ring and oxazine ring. In the case of thermosetting resins with benzoxazine ring in molecular structure, the oxazine ring is opened by heating and the polymerization proceeds without the formation of by-products. The benzoxazine-containing polybenzoxazines are attracting attention as a thermosetting resin for use in sealing materials, impregnation, laminates, adhesives, paints, coating materials, friction materials, FRP and molding materials.

These polybenzoxazines are known as cured polymers with well-balanced mechanical, electrical and chemical properties including high glass transition temperature (Tg), low dielectric characteristics, high tensile strength, low thermal expansion coefficient, excellent stretchability and low hygroscopicity, but have a disadvantage that they are cured at relatively high temperatures or cured slowly.

The use of various curing agents such as phenol (JP 2000-178332A), amine (JP 2000-86863A), and phosphine (JP 2003-82099A) for lowering the curing temperature of polybenzoxazine has been reported, and also alternative curing agents based on metal-ligand complexes have been reported. WO2008/034814 A2 discloses several modified acetylacetonate metal complexes as catalysts/curing agents for low temperature curing of benzoxazine-containing compositions.

However, some of the curing agents mentioned above are highly reactive and may lead to a partial polymerization of polybenzoxazine even at temperatures of 25° C. or less, and additionally, some of the curing agents mentioned above may negatively contribute to the thermal stability of polybenzoxazine or to the thermal stability of the curing reaction product of polybenzoxazine. As a result, there is a problem that undesired weight loss is caused, in particular during polymerization/curing reaction of polybenzoxazine.

Therefore, a novel mixture of polybenzoxazines is required which is rapidly cured at low temperature without the use of a curing agent and exhibits high thermal stability and low dielectric characteristics while maintaining excellent physical properties of polybenzoxazine.

PRIOR ART LITERATURE

Patent Literature

JP 2000-178332 A (2000 Jun. 27), Thermosetting resin composition.

JP2000-086863 A (2000 Mar. 28), Thermosetting resin composition.

JP2003-082099 (2003 Mar. 19), Thermosetting resin composition.

WO2008/0348142 (2008 Mar. 27), Benzoxazine-containing composition.

DISCLOSURE

Technical Problem

As a result of extensive studies in view of the above, the inventors of the present invention have made a benzoxazine-based mixture having a novel structure and identified that the mixture is excellent in dielectric constant, heat resistant characteristics and flame-retardant characteristics when cured after polymerization, thereby completing the present invention.

Accordingly, it is an object of the present invention to provide a benzoxazine-based mixture obtained by mixing a benzoxazine-based compound having a novel structure and a method for preparing the same.

In addition, it is another object of the present invention to provide a use of the polybenzoxazine cured product obtained by curing the benzoxazine-based mixture.

Technical Solution

In order to achieve the above objects, the present invention provides a benzoxazine-based mixture prepared by steps comprising:

(a) continuously reacting or condensing a hydroxyalkyl-phenol prepared by reaction of a phenol-based compound with a glyoxal with a phenol-based compound to prepare a multi-functional phenol-based mixture;

(b) mixing the multi-functional phenol-based mixture with a mono amine-based compound and (c) reacting the obtained mixture with an aldehyde-based compound.

In addition, the present invention also provides a thermosetting resin composition comprising the benzoxazine-based mixture.

In addition, the present invention provides a cured product comprising a polybenzoxazine obtained by curing the benzoxazine-based mixture.

Advantageous Effects

The benzoxazine-based mixture proposed in the present invention can produce a cured product having excellent dielectric constant, heat resistant characteristics and flame-retardant characteristics when cured.

The cured product has an advantage of excellent heat resistance and electrical characteristics while satisfying the physical properties required for a copper clad laminate used in a printed circuit board or a sealing material, a molding material, a template material, an adhesive or a material for the electric insulation paint used in an electronic part.

BEST MODE

The present invention provides a benzoxazine-based mixture of benzoxazine-based compounds having novel structures applicable to various fields, a method for preparing the same and a polybenzoxazine cured product obtained by curing the benzoxazine-based mixture.

The term 'halogen element' as used herein refers to F, Cl, Br, or I.

The term 'alkyl group' as used herein may include a linear or branched alkyl group, and for example, may include methyl, ethyl, propyl, 2-propyl, n-butyl, iso-butyl, tert-butyl, pentyl, hexyl, dodecyl, and the like, and when additionally substituted with halogen element, may include fluoromethyl, difluoromethyl, trifluromethyl, chloromethyl, dichloromethyl, trichloromethyl, iodomethyl, bromomethyl and the like. At this time, the alkenyl group is an alkyl group containing a double bond in a molecular structure and the alkynyl group is an alkyl group containing a triple bond.

The term 'cycloalkyl group' as used herein may include monocyclic, bicyclic or tricyclic, and may include, for example, cyclopropyl, cyclobutyl, cyclopentyl, cyclopentenyl, cyclohexyl, cyclohexenyl, cycloheptyl, cyclooctyl, decahydronaphthalenyl, adamantyl, norbornyl (i.e., bicyclo [2,2,1]hept-5-enyl) and the like.

The term 'alkoxy group' as used herein may include a hydroxy group (OH) in the molecular structure, and examples thereof may include methoxy, ethoxy, propoxy, isopropoxy, butoxy, pentoxy, heptoxy, dodecyloxy and the like, and when additionally substituted with halogen element, may include fluoromethoxy, difluoromethoxy, trifluoromethoxy, chloromethoxy, dichloromethoxy, trichloromethoxy, iodomethoxy, bromomethoxy and the like.

The terms 'aryl group' and 'arylene group' as used herein, unless otherwise specified, may have 6 to 60 carbon atoms, respectively, but are not limited thereto. In the present invention, the aryl group or the arylene group means a single ring or a multi-ring aromatic group and includes an aromatic ring which is formed when neighboring substituents are participated in a bond or a reaction. For example, the aryl group may be a phenyl group, a biphenyl group, a terphenyl group, a naphthyl group, an anthracenyl group, a fluorenyl group, a spirobifluorenyl group or a spirobifluorenyl group.

At this time, the prefix 'aryl' or 'ar' means a radical substituted with an aryl group. For example, the arylalkyl group is an alkyl group substituted with an aryl group, the arylalkenyl group is an alkenyl group substituted with an aryl group, and the radical substituted with an aryl group has the carbon number described in the present specification.

In the present specification, all the compounds or substituents may be substituted or unsubstituted unless otherwise specified. At this time, the term 'substituted' as used herein means that hydrogen is replaced by any one selected from the group consisting of a halogen atom, a hydroxy group, a carboxyl group, a cyano group, a nitro group, an amino group, a thio group, a methylthio group, an alkoxy group, a nitrile group, an aldehyde group, an epoxy group, an ether group, an ester group, a carbonyl group, an acetal group, a ketone group, an alkyl group, a perfluoroalkyl group, a cycloalkyl group, a heterocycloalkyl group, an allyl group, a benzyl group, an aryl group, a heteroaryl group, derivatives thereof and combinations thereof.

Benzoxazine-Based Mixture

The benzoxazine-based mixture of the present invention is a mixture of several kinds of benzoxazine-based compounds and is prepared by steps comprising (a) preparing a multi-functional phenol-based mixture; (b) mixing the multi-functional phenol-based mixture with a mono amine-based compound and (c) reacting the obtained mixture with an aldehyde-based compound.

Each step will be described in detail below.

Step (a): Preparing Step of Multi-Functional Phenol-Based Mixture

First, in step (a), hydroxyalkylphenol prepared by reaction of a phenol-based compound with glyoxal as a starting material is subjected to a continuous reaction or condensation reaction with a phenol-based compound to prepare a multi-functional phenol-based mixture.

The multi-functional phenol-based mixture means that two or more phenol functional groups are present in the molecular structure and may include a diphenol-based compound, a triphenol-based compound, a tetraphenol-based compound and a tetraphenol-based oligomer.

As an example, in the case of preparation of the multi-functional phenol-based mixture, 4-(1,2,2-trihydroxyethyl) phenol which is a hydroxyalkylphenol is prepared through the reaction of phenol with glyoxal as represented by the following reaction scheme 1. Then, in order to obtain the multi-functional phenol-based compound, it is then reacted continuously using a phenol-based compound or the resulting multi-functional phenol-based compounds are condensed.

[Reaction Scheme 1]

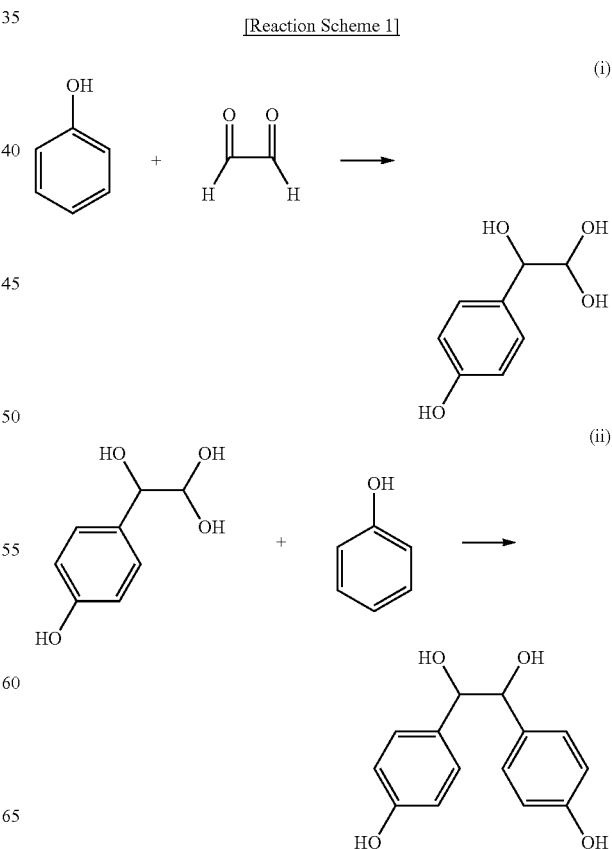

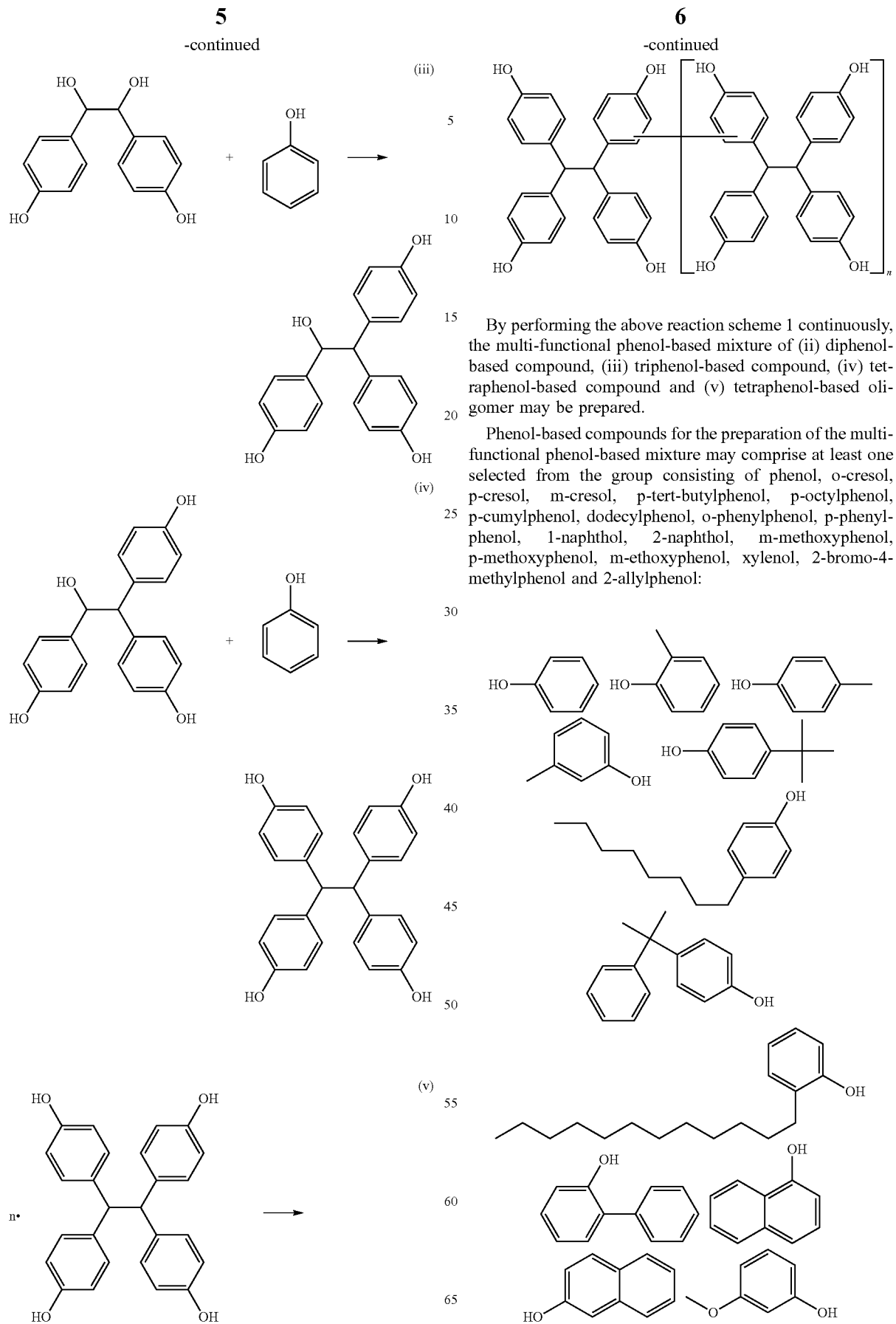

By performing the above reaction scheme 1 continuously, the multi-functional phenol-based mixture of (ii) diphenol-based compound, (iii) triphenol-based compound, (iv) tetraphenol-based compound and (v) tetraphenol-based oligomer may be prepared.

Phenol-based compounds for the preparation of the multi-functional phenol-based mixture may comprise at least one selected from the group consisting of phenol, o-cresol, p-cresol, m-cresol, p-tert-butylphenol, p-octylphenol, p-cumylphenol, dodecylphenol, o-phenylphenol, p-phenylphenol, 1-naphthol, 2-naphthol, m-methoxyphenol, p-methoxyphenol, m-ethoxyphenol, xylenol, 2-bromo-4-methylphenol and 2-allylphenol:

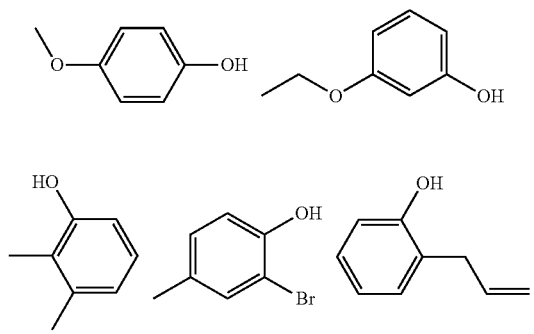

The multi-functional phenol-based mixture prepared from the phenol-based compounds may include a diphenol-based compound of formula 1, a triphenol-based compound of formula 2, a tetraphenol-based compound of formula 3 and a tetraphenol oligomer of formula 4 as represented below:

[Formula 1]

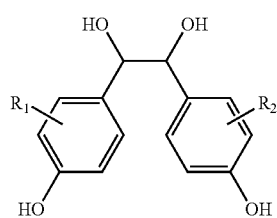

[Formula 2]

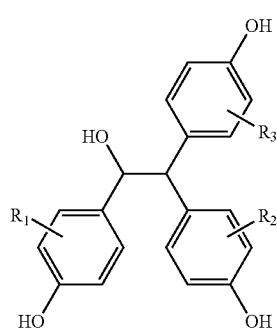

[Formula 3]

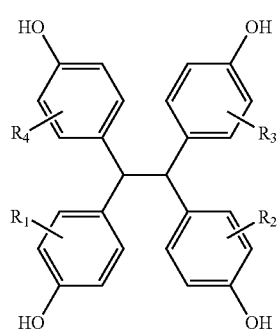

[Formula 4]

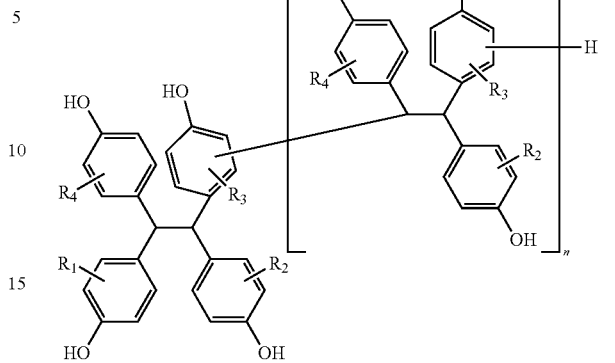

wherein $R_1$ to $R_4$ are the same or different from each other and each independently are H, halogen element, a carboxyl group, a C1 to C20 alkyl group, a C3 to C20 cycloalkyl group, a C2 to C20 alkenyl group, a C2 to C20 alkynyl group, a C2 to C20 alkoxy group, a C6 to C20 aryl group, a C7 to C20 aralkyl group, or an allyl group, wherein the aryl group comprises a fused ring and n is an integer of 1 to 15.

n is an index associated with the tetraphenol-based oligomer. When n is 1, the compound is referred to as a tetraphenol-based dimmer, when n is 2, the compound is referred to as a tetraphenol-based trimer, when n is 3, the compound is referred to as a tetraphenol-based tetramer, when n is greater than 3 and the compound is referred to as a higher order oligomer. Preferably, n is an integer from 1 to 15, more preferably an integer from 1 to 10, most preferably an integer from 1 to 4.

In addition, $R_1$ to $R_4$ may substitute for one or two or more hydrogen atoms in the phenyl ring. When substituted by two or more functional groups, they may be the same functional group or different functional groups. For example, it is possible to be substituted by dimethyl group, methyl group/bromine and the like, respectively.

At this time, the reaction is not proceeded in such a way that the multi-functional phenol-based compound prepared in each step is separated and then reacted with the phenol-based compound, but after the reaction in one step is completed, the next step is proceeded without any separation process. Accordingly, since at least two kinds of multi-functional phenolic compounds having the structures of formulas 1 to 4 are used in mixture, benzoxazine-based compounds having different structures are prepared even when reacting with mono amine-based compounds and aldehyde-based compounds, and the finally obtained form is present in a mixed state of at least two kinds of benzoxazine-based compounds.

Preferably, the multi-functional phenol-based mixture of the present invention may comprise an amount of (ii) from 2 to 8% by weight of the diphenol based compound, (iii) from 10 to 30% by weight of the triphenol based compound, (iv) form 12 to 45% by weight of the tetraphenol-based compound and (v) from 40 to 70% by weight of the tetraphenol-based oligomer based on the total weight of the composition and in addition to these, further contains various remaining by-products or unreacted materials.

These multi-functional phenol-based mixtures may react with subsequent monoamine-based compounds and aldehyde-based compounds to form oxazine rings. Particularly, in the preparation of the benzoxazine-based mixture of the present invention, since compounds having a single structure are not used as phenol-based compounds but various multi-functional phenolic compounds having the structures of formulas 1 to 4 are used in mixture, benzoxazine-based compounds having different structures from each other may be prepared even when reacting with mono amine-based compounds and aldehyde-based compounds and the finally obtained form is present in a mixed state of the above compounds.

The reaction of a phenol-based compound having the above structure with a glyoxal and further reaction with a phenol-based compound, may be carried out in the presence of an acid catalyst. The acid which can be used is not limited to the present invention and any acid catalyst can be used as long as it is a known acid catalyst. Typically, the acid catalyst may be one selected from sulfuric acid, nitric acid, hydrochloric acid, acetic acid, para-toluene sulfonic acid, methyl sulfonic acid, boron trifluoride, aluminum chloride and sulfonic acid, and preferably, sulfuric acid may be used.

Also, the reaction of each step may be carried out at from 70 to 90° C. for from 1 to 5 hours and a vacuum degassing process may be performed to remove unreacted substances after the reaction.

Step (b): Mixing Step of Multi-Functional Phenol-Based Mixture and Mono Amine-Based Compound Next, in step (b), a multi-functional phenol-based mixture and a mono amine-based compound are mixed.

The mono amine-based compound may be any compound as long as it can react with multi-functional phenol-based mixture to form benzoxazine ring. For example, the mono amine-based compound may comprise selected from the group consisting of ethanolamine, allylamine, methylamine, ethylamine, propylamine, butylamine, isopropylamine, hexylamine, octadecylamine, cyclohexylamine, 2-aminofluorene and aniline, and it may be preferable to select an allylamine or aniline in terms of reactivity and ease of production.

The reaction may be carried out by adding a mono amine-based compound to the multi-functional phenol-based compound, wherein the mono amine-based compound may be added and reacted at a molar ratio of from 2 to 8 mol relative to 1 mol of the multi-functional phenol-based mixture and also for stable reactions, the mono amine-based compound can be used in slightly over the above molar ratio.

Step (c): Reaction with Aldehyde-Based Compound

An aldehyde-based compound is added to the mixture obtained in the step (b) and then reacted to prepare a benzoxazine-based mixture.

The aldehyde-based compounds may comprise formaldehyde, acetaldehyde, propionaldehyde, butylaldehyde, paraformaldehyde, polyoxymethylene and the like. It may be preferable to use formaldehyde and paraformaldehyde in terms of reactivity and economy. Preferably, a 40% aqueous formaldehyde solution may be slowly added over a period of 30 minutes to 120 minutes.

At this time, the aldehyde-based compound may be added in a molar ratio of from 6 to 18 mol, preferably from 8 to 16 mol, relative to 1 mol of the multi-functional phenol-based mixture in step (a). When the amount of aldehyde used is less than the above-mentioned molar ratio, it does not induce sufficient reaction with mono amine-based compound, and thus oxazine ring is not formed and heat resistance is deteriorated. On the contrary, when the content of aldehyde used is higher than the above molar ratio, thermal characteristics, electrical characteristics and dimensional stability are deteriorated due to side reactions.

Examples of the solvent used in the reaction may be aromatic hydrocarbon-based solvents such as toluene, xylene, trimethylbenzene and the like; halogen-based solvents such as chloroform, dichloroform, and dichloromethane; ether-based solvents such as THF and dioxane, and the like. At this time, the content of the solvent may be preferably from 25 to 100 parts by weight based on 100 parts by weight of the total content of the multi-functional phenol-based mixture, the monoamine-based compound and the aldehyde-based compound.

In the preparation of the benzoxazine, when the content of the solvent is too small, the viscosity of the reactant is increased and thus the stirring stress is increased, thereby resulting in poor workability. When the content of the solvent is excessive, the cost for removing the solvent after the reaction becomes high, which may be uneconomical. In addition, when proper solvent selection and mixing reactions are not properly performed, the yield may be lowered because the raw materials do not participate in the reaction.

The reaction in step (c) may be carried out with stirring for from 30 minutes to 120 minutes while maintaining the temperature between from 40 and 80° C., preferably between from 55 and 65° C. When the reaction is carried out in the above conditions, the ring closing reaction (oxazine formation) can be effectively performed.

Since the mixture proposed in the present invention is the multi-functional phenol-based mixture which has a form in which (ii) a diphenol-based compound, (iii) a triphenol-based compound, (iv) a tetraphenol-based compound and (v) a tetraphenol-based oligomer coexist, the finally prepared benzoxazines are not a single compound but exist as a mixture of various types of the benzoxazine compounds derived from (ii) to (v) above.

Preferably, the benzoxazine-based mixture may include at least two selected from the group consisting of a dibenzoxazine-based compound of formula 5, a tribenzoxazine-based compound of formula 6, a tetrabenzoxazine-based compound of formula 7, and a tetrabenzoxazine oligomer of formula 8 as represented below:

[Formula 5]

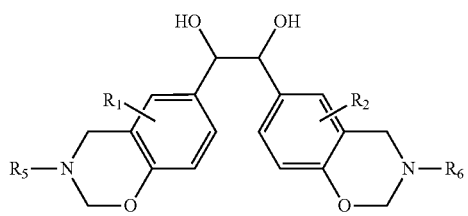

[Formula 6]

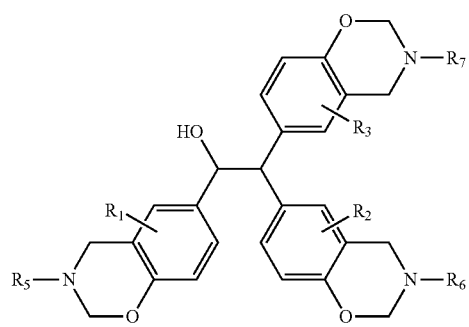

[Formula 7]

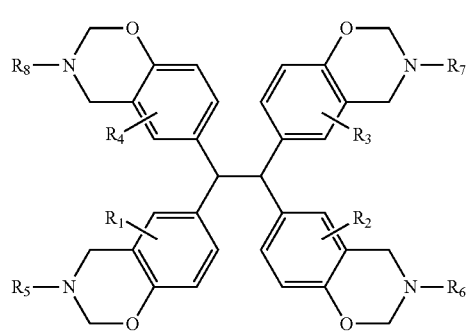

[Formula 8]

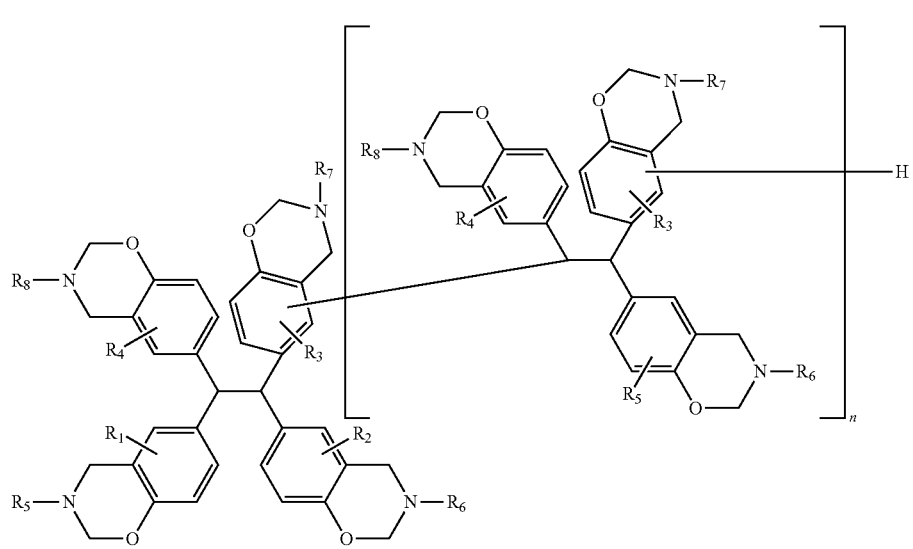

wherein $R_1$ to $R_4$ and n are as described above and $R_5$ to $R_8$ are the same or different from each other and each independently are a C1 to C20 alkyl group, a C3 to C20 cycloalkyl group, an allyl group, a C3 to C20 alkenyl group, a C3 to C20 alkynyl group, a C6 to C20 aryl group, a C7 to C20 aralkyl group, wherein functional group is substituted or unsubstituted with halogen.

Preferably, $R_1$ to $R_4$ may be H, Br, Cl, a C1 to C12 alkyl group, a C1 to C12 alkoxy group, a C6 to C12 aryl group or an allyl group, more preferably H, a methyl group, an ethyl group, propyl group, a t-butyl group, a hexyl group, an octyl group, an octadecyl group, a dodecyl group, a cumyl group, a phenyl group, a fused phenyl group, a methoxy group, an ethoxy group, a bromomethyl group or an allyl group.

Preferably, $R_5$ to $R_8$ may be H, a C1 to C12 alkyl group, a C2 to C12 alkenyl group, a C1 to C12 alkoxy group, a C4 to C10 cycloalkyl group, a C6 to C12 aryl group or an allyl group, more preferably a methyl group, an ethyl group, a butyl group, a propenyl group, a cyclohexyl group, a phenyl group, a naphthyl group, an allyl group, a fluorenyl group, a fluorobenzyl group.

More preferably, the benzoxazine-based mixture of the present invention may include the following compounds, and preferably may include two or more of these compounds, more preferably all four of these compounds:

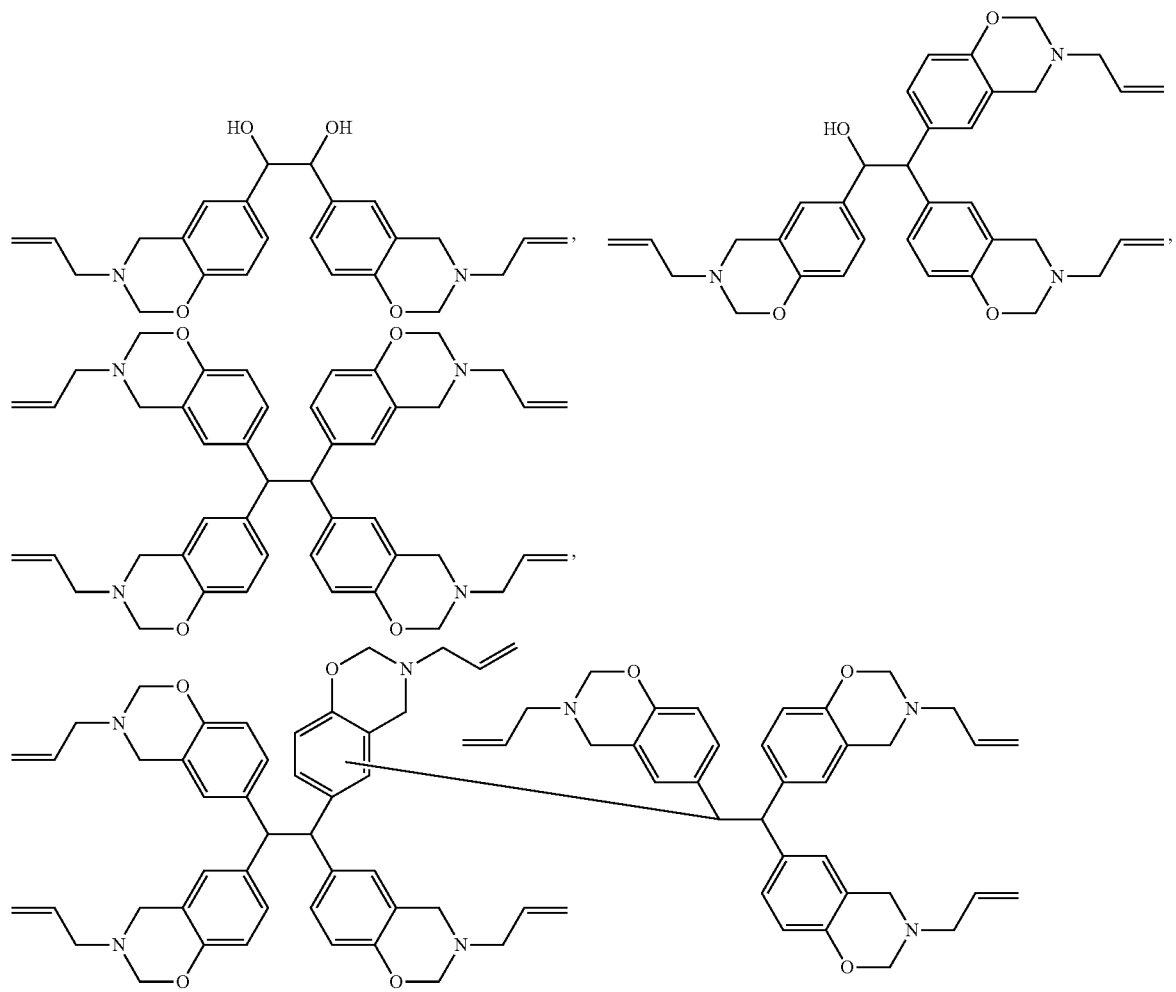
40
In addition, the benzoxazine-based mixture of the present invention may include the following compounds, and preferably may include two or more of these compounds, more preferably all four of these compounds:
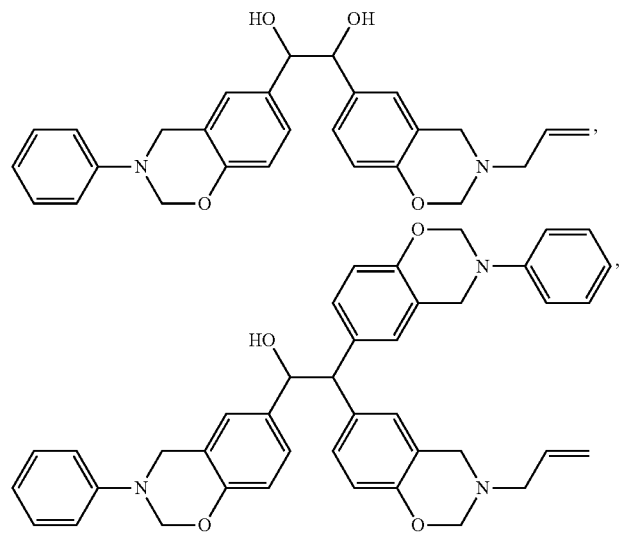

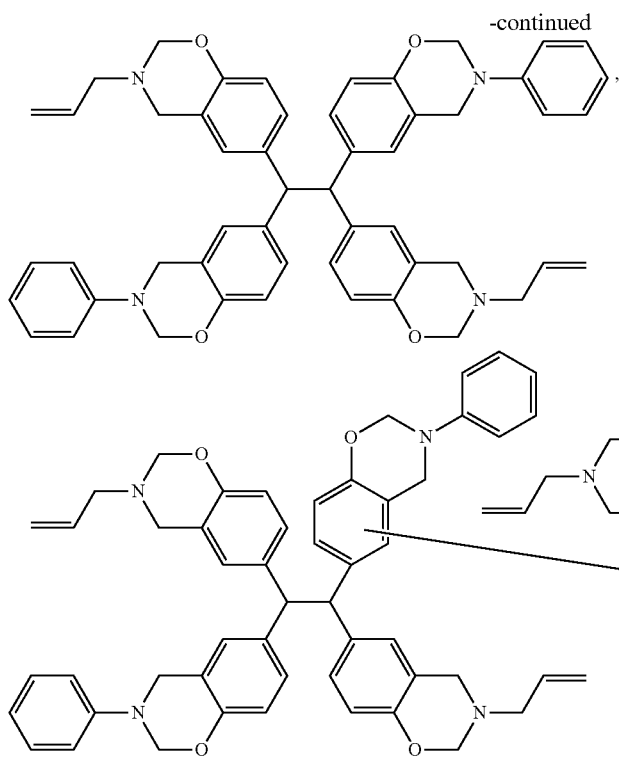

The benzoxazine-based mixture mentioned above may comprise an amount of (ii) from 2 to 8% by weight of the dibenzoxazine-based compound, (iii) from 10 to 30% by weight of the tribenzoxazine-based compound, (iv) from 12 to % by weight of the tetrabenzoxazine-based compound and (v) from 40 to 70% by weight of the tetrabenzoxazine-based oligomer based on the total weight of the composition and in addition to these, further contains various remaining by-products or unreacted materials.

The benzoxazine-based mixtures can be applied to various fields. For example, by applying alkyl phenol and fatty acid amine compound, the free volume inside the structure of benzoxazine can be increased and thus it is possible to obtain an effect of improving dielectric characteristics and improving heat resistance at the same time.

Polybenzoxazine Cured Product and its Use

The benzoxazine-based mixture according to the present invention is capable of preparing a polybenzoxazine cured product through a curing reaction.

The curing may take place by opening the oxazine ring in the benzoxazine ring, thereby forming a cured product. At this time, the term 'cured product' does not mean only a self-cured product of a polybenzoxazine solely, but may be meant to encompass a product cured by mixing other resin-based compositions in addition to the polybenzoxazine precursor resin.

The curing process may be performed through thermal curing, for example, at a temperature in the range of from 150 to 250° C., and more preferably at from 190 to 220° C. When the temperature is lower than 150° C., the curing time may be excessively long. When the temperature is higher than 250° C., oxidation of the impurities may be excessively induced and excessive energy may be consumed during the process. Particularly, in the range of from 190 to 220° C., it is more preferable in view of process time, energy efficiency and the like.

Since the polybenzoxazine cured product prepared by the above-described method may have a structure favorable for low dielectric characteristics of dielectric constant (Dk) of 2.7 and dielectric tangent (dissipation factor: Df) of 0.01 or less, it may have excellent electrical characteristics while maintaining excellent heat resistance, and thus can be used for a copper clad laminate used in a printed circuit board, or a sealing material, a molding material, a template material, an adhesive, or a material for the electric insulation paint used in an electronic part because of those properties At this time, the benzoxazine-based mixture may be prepared in the form of a thermosetting resin composition comprising the same and the resin composition may further include various resins and additives suitable for each application.

Hereinafter, the present invention will be described in more detail with reference to examples. It will be apparent to those skilled in the art to which the present invention pertains that these examples are only for illustrating the present invention more specifically, and the scope of the present invention is not limited by these examples.

EXAMPLES

Example 1: Preparation of Benzoxazine-Based Mixture A (1) Preparation of Benzoxazine-Based Mixture A 2400 g (11.96 mol) of phenol and 443 g (7.63 mol) of glyoxal were added to a three-necked flask purged with nitrogen and stirred, and then 1.2 g (0.012 mol) of $H_2SO_4$ was added thereto. Then, the temperature inside the reactor was raised to 90° C. and the reaction was carried out for 2 hours. Subsequently, vacuum degasification was performed for 2 hours or longer to remove the side reaction product. After completion of the reaction, the temperature in the reactor was gradually cooled, and 1.536 g of 50% NaOH was added to neutralize it. Next, vacuum degasification was performed up to 120° C. to sufficiently recover unreacted materials.

1800 g of water was added to the recovered product, and the mixture was sufficiently stirred at 60° C., and the mixture was allowed to stand to remove the water phase portion in the upper layer portion and recover the oil phase portion in the lower layer portion. The oil phase portion was vacuum-degassed to 170° C., then the vacuum was released, and steam streaming was performed at 160° C. for 3 hours or more. Subsequently, the temperature was raised to 170° C. again and vacuum degasification was carried out to prepare a multi-functional phenol-based mixture.

Next, 840 g (8.1 mol) of the synthesized tetraphenyl ethane was dissolved in 435.87 g (7.68 mol) of toluene and 1160.4 g of allylamine in a 3 L three-necked flask purged with nitrogen. 1154.25 g (15.3 mol) of a 40% aqueous solution of formaldehyde was then added while maintaining the temperature in the flask at 55° C.

The reaction solution was heated to 100° C. and azeotropic distillation was carried out. After the dehydration was completed, the reaction solvent was completely removed by vacuum degasification, and the title compound was obtained through fractional distillation.

(2) Analysis and Result

The contents of the multi-functional phenol-based mixture prepared in (1) above and the final obtained benzoxazine-based mixture were measured by performing gel permeation chromatography (GPC, Waters 707 instrument) and analyzing the peaks and the obtained results are shown in tables 1 and 2 below.

TABLE 1

| Structure | Content |
|---|---|
| (structure) | 3.38% by weight |

TABLE 1-continued

| Structure | Content |
|---|---|
| (structure) | 23.75% by weight |
| (structure) | 36.99% by weight |
| (structure) | 34.09% by weight |

TABLE 2

| Structure | Content |
|---|---|
| (structure) | 4.6% by weight |

TABLE 2-continued

| Structure | Content |
|---|---|
| [structure] | 16.7% by weight |
| [structure] | 16.7% by weight |
| [structure] | 60.2% by weight |

Example 2: Preparation of Benzoxazine-Based Mixture B (1) Preparation of Benzoxazine-Based Mixture B 2400 g (11.96 mol) of phenol and 443 g (7.63 mol) of glyoxal were added to a three-necked flask purged with nitrogen and stirred, and then 1.2 g (0.012 mol) of $H_2SO_4$ was added thereto. Then, the temperature inside the reactor was raised to 90° C. and the reaction was carried out for 2 hours. Subsequently, vacuum degasification was performed for 2 hours or longer to remove the side reaction product. After completion of the reaction, the temperature in the reactor was gradually cooled, and 1.536 g of 50% NaOH was added to neutralize it. Next, vacuum degasification was performed up to 120° C. to sufficiently recover unreacted materials.

1800 g of water was added to the recovered product, and the mixture was sufficiently stirred at 60° C., and the mixture was allowed to stand to remove the water phase portion in the upper layer portion and recover the oil phase portion in the lower layer portion. The oil phase portion was vacuum-degassed to 170° C., then the vacuum was released, and steam streaming was performed at 160° C. for 3 hours or more. Subsequently, the temperature was raised to 170° C. again and vacuum degasification was carried out.

Next, 700 g (6.77 mol) of the synthesized tetraphenyl ethane was dissolved in 1124.4 g of toluene and 182.7 g (3.2 mol) of allylamine in a 3 L three-necked flask purged with nitrogen. 966.98 g (12.88 mol) of a 40% aqueous solution of formaldehyde was then added while maintaining the temperature in the flask at 55° C.

The reaction solution was heated to 100° C. and azeotropic distillation was carried out. After the dehydration was completed, the reaction solvent was completely removed by vacuum degasification, and the title compound was obtained through fractional distillation.

(2) Analysis and Result

The contents of the final obtained benzoxazine-based mixture were measured by performing gel permeation chromatography (GPC, Waters 707 instrument) and analyzing the peaks and the obtained results are shown in tables 3 below.

TABLE 3

| Structure | Content |
|---|---|
| 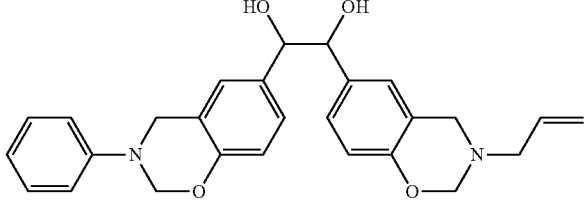 [SMILES: C=CCN1COc2ccc(C(O)C(O)c3ccc4c(c3)CN(c3ccccc3)CO4)cc2C1] | 16.04% by weight |
| 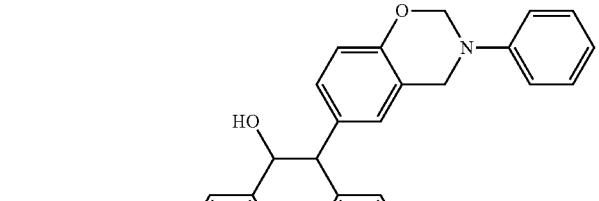 | 5.72% by weight |
| 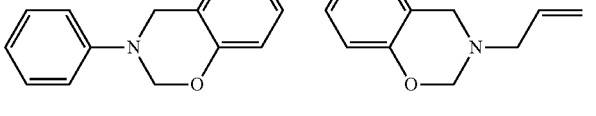 | 20.2% by weight |
| 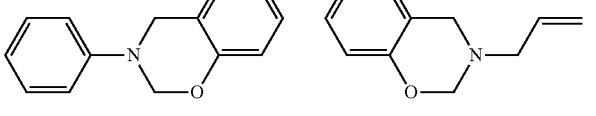 | 51.2% by weight |

Comparative Example 1: Preparation of Benzoxazine-Based Compound 484.2 g of toluene was added to a 3 L three-necked flask purged with nitrogen, and 652.71 g (2.0 mol) of aniline and 800 g (1 mol) of bisphenol A were added thereto. When the addition was completed, the reaction solution was heated to 100° C. at a temperature raising rate of 1.3° C./min and stirred for 5 hours. Thereafter, the temperature was raised to 120° C., and the solvent was completely removed at a pressure of 10 torr for 60 minutes to prepare 1500 g of a benzoxazine monomer having a weight average molecular weight of 698 g/mol. The obtained benzoxazine contained 54.26% by weight of the benzoxazine monomer represented by formula 9 below and the yield (relative to the theoretical yield according to the equivalent ratio of the reaction solution) was 92%.

[Formula 9]

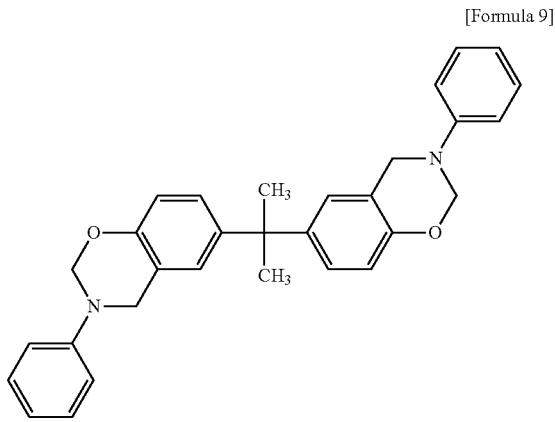 [SMILES: CC(C)(c1ccc2c(c1)CN(c1ccccc1)CO2)c1ccc2c(c1)CN(c1ccccc1)CO2]

Comparative Example 2: Preparation of Benzoxazine-Based Compound 514.7 g of toluene was added to a 3 L three-necked flask purged with nitrogen, and 744.18 g (2.0 mol) of aniline and 800 g (1 mol) of bisphenol F were added thereto. When the addition was completed, the reaction solution was heated to 100° C. at a temperature raising rate of 1.3° C./min and stirred for 5 hours. Thereafter, the temperature was raised to 120° C., and the solvent was completely removed at a pressure of 10 torr for 60 minutes to prepare 945 g of a benzoxazine monomer having a weight average molecular weight of 1240 g/mol. The obtained benzoxazine contained 22.58% by weight of the benzoxazine monomer represented by formula 10 below and the yield (relative to the theoretical yield according to the equivalent ratio of the reaction solution) was 93%.

[Formula 10]

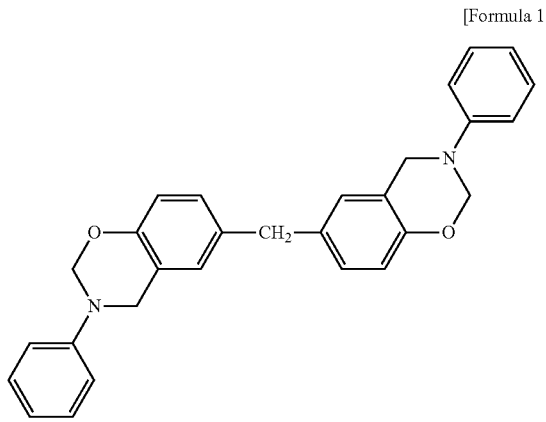

Experimental Example 1

The benzoxazine-based mixtures and compounds obtained in the above examples and comparative examples were impregnated with glass fibers, naturally dried at room temperature for 1 hour, and then dried in an oven at 155° C. for 5 minutes to prepare a prepreg.

The prepared prepregs of 8 ply was prepared by pressing at 195° C. under the pressure of 40 kgf/cm$^2$ for 120 minutes along with copper foil (1 once) in front and back.

The properties obtained at this time were measured on the basis of the following contents, and the results were shown in table 4 below.

Property Evaluation Method (1) Measurement of Glass Transition Temperature (° C.)

The copper clad laminate prepared above was cut to a size of 5 cm×1 cm to obtain a specimen. The obtained specimen was measured by dynamic mechanical analysis (DMA) and measured at a heating rate of 3° C. per minute from 30° C. to 350° C. using a TA Instruments DMA Q800.

(2) Measurement of Dielectric Constant

The dielectric constant (Dk) and dielectric tangent (Df) of the copper clad laminate was measured using an Agilent impedance analyzer (Agilent E4991A 1 MHz to 3 GHz) under the following conditions.

Measurement frequency: 1 GHz
Measurement temperature: 25~27° C.
Measurement humidity: 45-55%
Measurement sample: thickness 1.5 mm (1.3~1.7 mm)

(3) Measurement of Weight Average Molecular Weight (Mw)

The weight average molecular weight (Mw) in terms of polystyrene was determined by gel permeation chromatography (GPC) (Waters: Waters 707). The polymer to be measured was dissolved in tetrahydrofuran so as to have a concentration of 4000 ppm, and 100 $\mu\ell$ of solution was injected into GPC. Tetrahydrofuran was used as the mobile phase of GPC and flowed at a flow rate of 1.0 mL/min and analysis was performed at 35° C. As columns, four Waters HR-05,1,2, and 4E columns were connected in series. Detectors were RI and PAD Detecter, and detection was performed at 35° C.

TABLE 4

|  | Example 1 | Example 2 | Comparative Example 1 | Comparative Example 2 |
| --- | --- | --- | --- | --- |
| Tg(° C.) | >300 | 287 | 198.7 | 195.9 |
| Dk | 2.53 | 2.62 | 3.00 | 3.45 |
| Df | 0.005 | 0.006 | 0.01 | 0.015 |
| Mw(g/mol) | 1589 | 1124 | 698 | 1240 |

Through the above results, it can be seen that when a polybenzoxazine cured product prepared by the present invention is included, it is possible to produce a copper clad laminate having a high Tg and low dielectric characteristics.

The invention claimed is:

1. A benzoxazine-based mixture prepared by steps comprising:
   (a) continuously reacting or condensing a hydroxyalkyl-phenol prepared by reaction of a phenol-based compound and a glyoxal with a phenol-based compound to prepare a multi-functional phenol-based mixture;
   (b) mixing the multi-functional phenol-based mixture with a mono amine-based compound and
   (c) reacting the obtained mixture with an aldehyde-based compound,
   wherein the mono amine-based compound is a mono-amine compound capable of reacting with the multi-functional phenol-based mixture to form benzoxazine ring,
   wherein the aldehyde-based compound comprises at least one selected from the group consisting of formaldehyde, acetaldehyde, propionaldehyde and butylaldehyde, wherein the benzoxazine-based mixture comprises at least two selected from a dibenzoxazine-based compound of formula 5, a tribenzoxazine-based compound of formula 6, a tetrabenzoxazine-based compound of formula 7 and a tetrabenzoxazine-based oligomer of formula 8 as represented below:

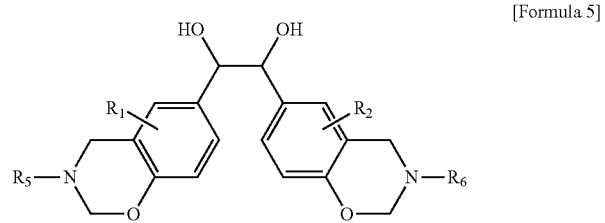
[Formula 5]

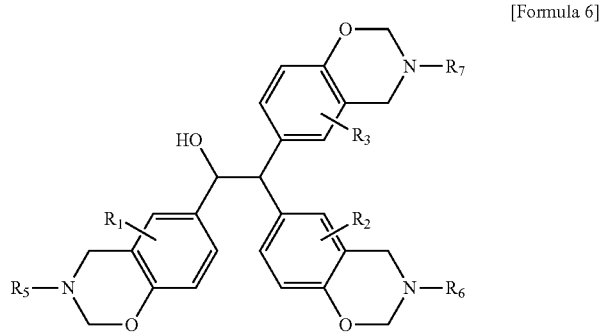
[Formula 6]

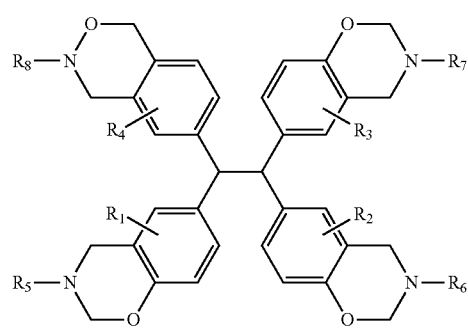
[Formula 7]

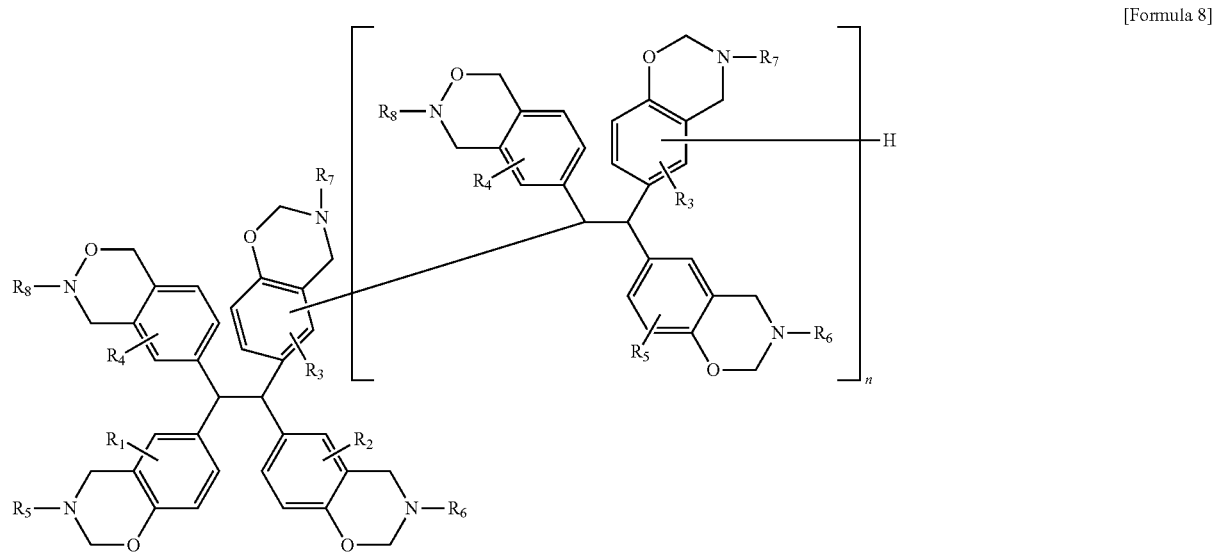
[Formula 8]

wherein $R_1$ to $R_4$ are the same or different from each other and each independently are H, halogen element, a carboxyl group, a C1 to C20 alkyl group, a C3 to C20 cycloalkyl group, a C2 to C20 alkenyl group, a C2 to C20 alkynyl group, a C2 to C20 alkoxy group, a C6 to C20 aryl group, a C7 to C20 aralkyl group, or an allyl group, wherein the aryl group comprises a fused ring, n is an integer of 1 to 15, and $R_5$ to $R_8$ are the same or different from each other and each independently are a C1 to C20 alkyl group, a C3 to C20 cycloalkyl group, an allyl group, a C3 to C20 alkenyl group, a C3 to C20 alkynyl group, a C6 to C20 aryl group, a C7 to C20 aralkyl group, wherein functional groups are substituted or unsubstituted with halogen.

2. The benzoxazine-based mixture according to claim 1, wherein the phenol-based compound comprises at least one selected from the group consisting of phenol, o-cresol, p-cresol, m-cresol, p-tert-butylphenol, p-octylphenol, p-cumylphenol, dodecylphenol, o-phenylphenol, p-phenylphenol, 1-naphthol, 2-naphthol, m-methoxyphenol, p-methoxyphenol, m-ethoxyphenol, xylenol, 2-bromo-4-methylphenol and 2-allylphenol.

3. The benzoxazine-based mixture according to claim 1, wherein the multi-functional phenol-based mixture comprises at least two of a diphenol-based compound of formula 1, a triphenol-based compound of formula 2, a tetraphenol-based compound of formula 3 and a tetraphenol oligomer of formula 4 as represented below:

[Formula 1]

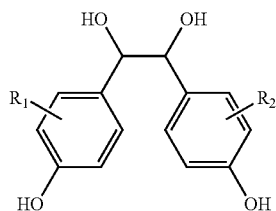

[Formula 2]

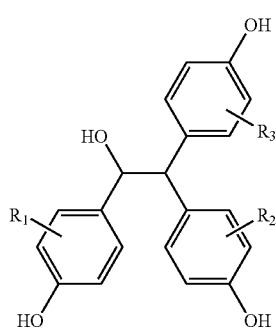

[Formula 3]

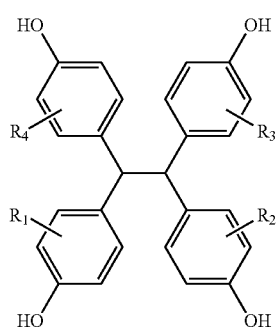

[Formula 4]

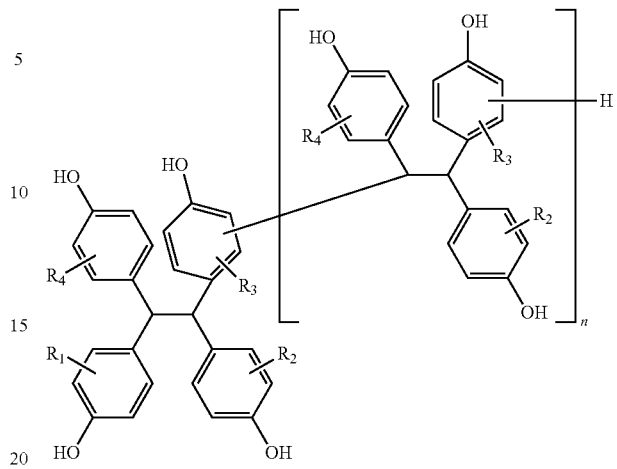

wherein $R_1$ to $R_4$ are the same or different from each other and each independently are H, halogen element, a carboxyl group, a C1 to C20 alkyl group, a C3 to C20 cycloalkyl group, a C2 to C20 alkenyl group, a C2 to C20 alkynyl group, a C2 to C20 alkoxy group, a C6 to C20 aryl group, a C7 to C20 aralkyl group, or an allyl group, wherein the aryl group comprises a fused ring, and n is an integer of 1 to 15.

4. The benzoxazine-based mixture according to claim 1, wherein the reaction of step (a) is carried out at from 70 to 90° C. under an acid catalyst.

5. The benzoxazine-based mixture according to claim 4, wherein the acid catalyst comprises at least one selected from sulfuric acid, nitric acid, hydrochloric acid, acetic acid, para-toluene sulfonic acid, methyl sulfonic acid, boron trifluoride, aluminum chloride and sulfonic acid.

6. The benzoxazine-based mixture according to claim 1, wherein the mono amine-based compound comprises at least one selected from the group consisting of ethanolamine, allylamine, methylamine, ethylamine, propylamine, butylamine, isopropylamine, hexylamine, octadecylamine, cyclohexylamine, 2-aminofluorene and aniline.

7. The benzoxazine-based mixture according to claim 1, wherein the reaction of step (c) is carried out at from 40 to 80° C.

8. The benzoxazine-based mixture according to claim 1, wherein the benzoxazine-based mixture comprises at least two benzoxazine-based compounds selected from the following compounds:

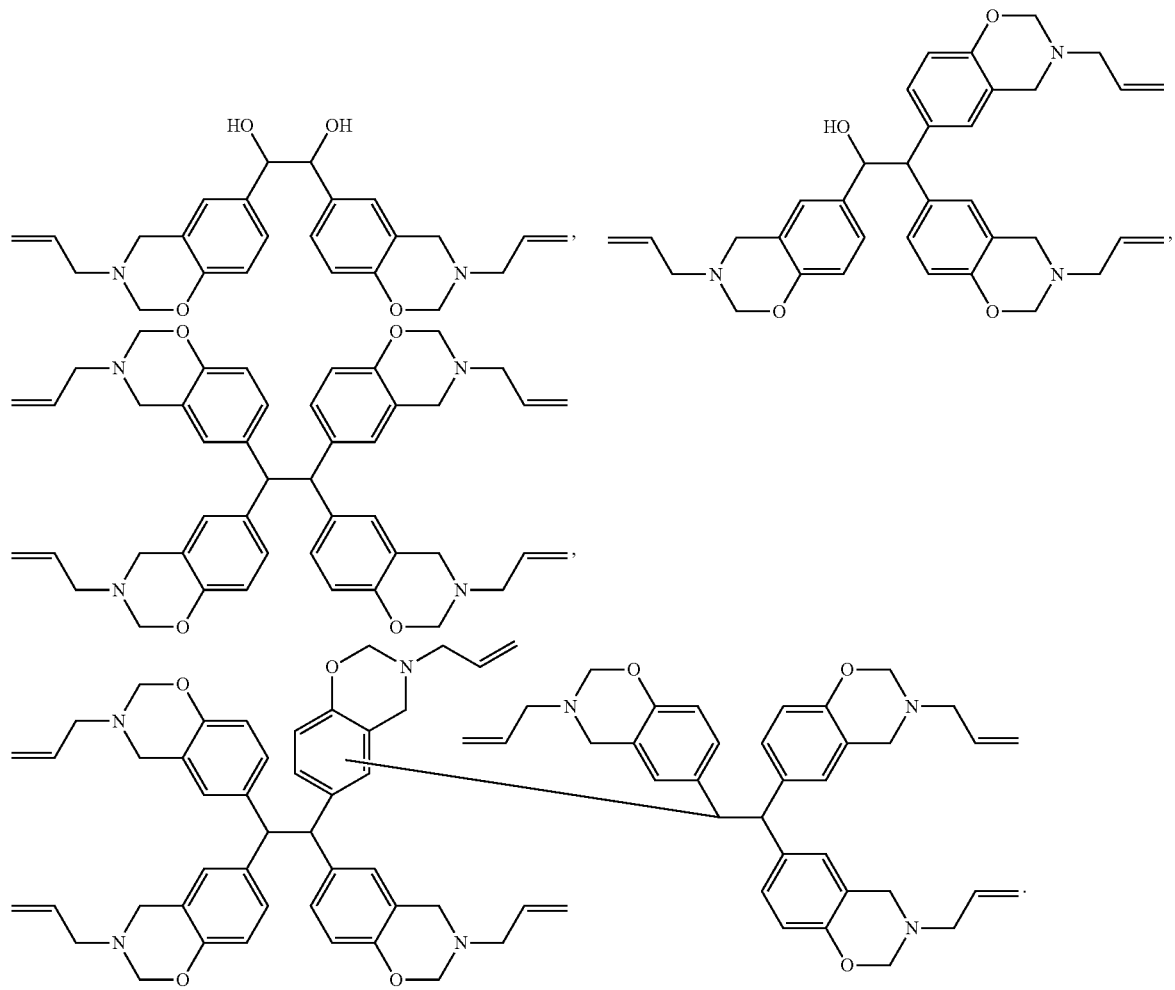
9. The benzoxazine-based mixture according to claim 1, wherein the benzoxazine-based mixture comprises at least two benzoxazine-based compounds selected from the following compounds:
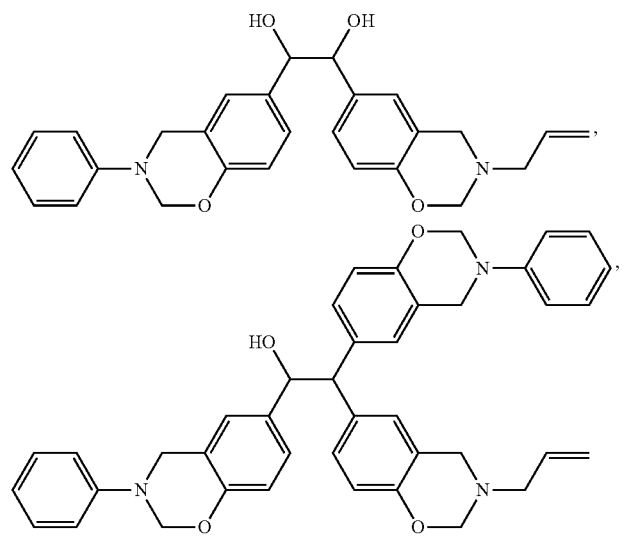

-continued
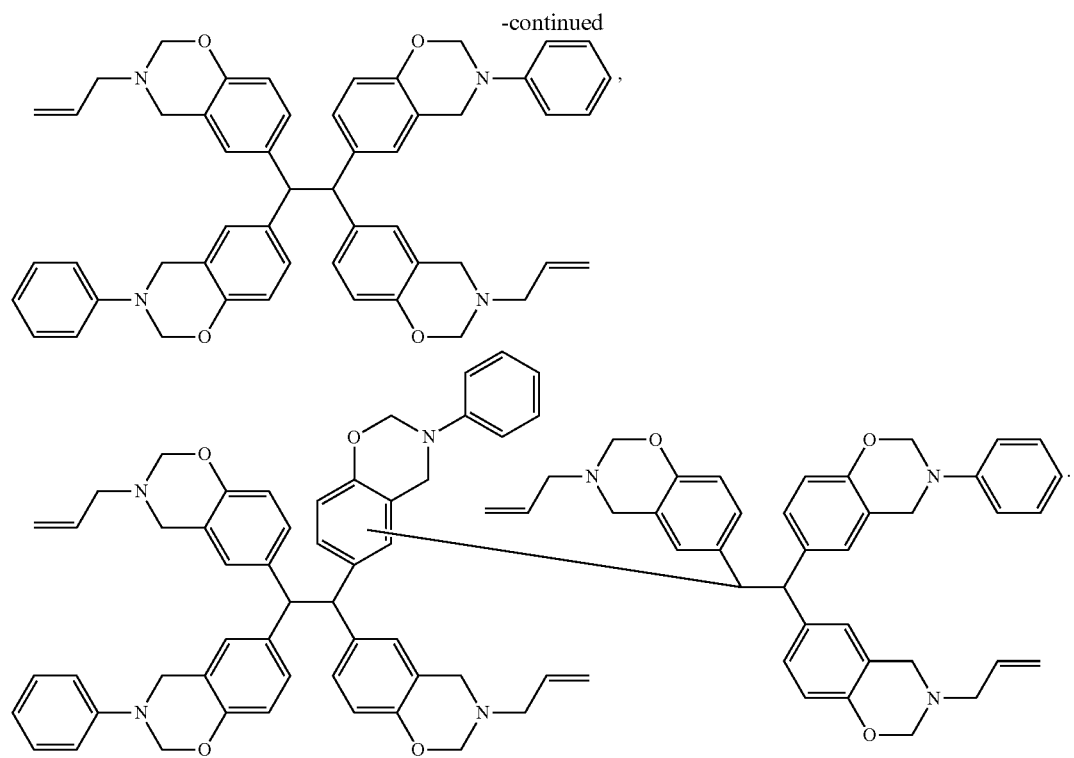
10. A thermosetting resin composition comprising the benzoxazine-based mixture according to claim 1.
11. A cured product comprising a polybenzoxazine cured from the benzoxazine-based mixture according to claim 1.
\* \* \* \* \*